United States Patent [19]
Qiu et al.

[11] Patent Number: 6,033,685
[45] Date of Patent: Mar. 7, 2000

[54] TABLET FOR THE CONTROLLED RELEASE OF ACTIVE AGENTS

[75] Inventors: Yihong Qiu, Gurnee; Jay S. Trivedi, Skokie; Sharon L. Graham, Roselle; Kolette M. Flood, Crystal Lake; Steven L. Krill, Gurnee, all of Ill.

[73] Assignee: Abbott Laboratories, Abbott Park, Ill.

[21] Appl. No.: 09/106,658

[22] Filed: Jun. 29, 1998

Related U.S. Application Data

[63] Continuation-in-part of application No. 08/781,761, Jan. 10, 1997.
[51] Int. Cl.$^7$ .................................................. A61K 9/20
[52] U.S. Cl. .................... 424/464; 424/468; 424/469; 424/470; 424/472; 424/474; 424/475
[58] Field of Search ........................... 424/464, 468, 424/469, 470, 472, 474, 475

[56] References Cited

U.S. PATENT DOCUMENTS

4,756,911  7/1988  Drost et al. ............................. 424/468

Primary Examiner—Jose' G. Dees
Assistant Examiner—Kathryne E. Shelborne
Attorney, Agent, or Firm—Mona Anand; Portia Chen

[57] ABSTRACT

The present invention provides a tablet for the controlled release of an active agent comprising (a) a matrix layer comprising an active agent embedded in a non-swelling, non-gelling hydrophobic matrix; (b) a first barrier layer laminated to a single face of the matrix layer; and (c) an optional second barrier layer laminated to the opposite face of the matrix layer and oppositely disposed to the first barrier layer; wherein the matrix comprises up to about 80% active agent and from about 5% to about 80% by weight of nonswellable waxes or polymeric material insoluble in aqueous medium, and the first and second barrier layers independently comprise (1) polymeric material exhibiting a high degree of swelling and gelling in aqueous medium or (2) nonswellable wax or polymeric material insoluble in aqueous medium.

19 Claims, 5 Drawing Sheets

TABLET FOR THE CONTROLLED RELEASE OF ACTIVE AGENTS

TECHNICAL FIELD

The present invention is a continuation-in-part under 37 C.F.R. 1.53(b) of U.S. application Ser. No. 08/781,761, filed Jan. 10, 1997. The invention relates to a device for the controlled release of an active substance. More particularly, it relates to a layered tablet whose properties are such that it releases the active substance at a constant rate over a significant time period.

BACKGROUND OF THE INVENTION

Many delivery systems for the delayed or controlled release of an active substance are currently available. Some state of the art delayed or controlled release systems can be described as membrane controlled systems, which are summarized and described in Robinson & Lee, *Controlled Drug Delivery*, Mercel Dekker, Inc., New York (1989), pp. 373–421. As the name suggests, these systems comprise a medicament-containing core wherein a membrane or coating encasing the core controls release of the medicament from the system. Typically, these systems give rise to controlled drug release by pores produced in a partially water-soluble polymer. Lieberman, Lachman, & Schwartz, *Pharmaceutical Dosage Forms*, Mercel Dekker, Inc., New York (1991), pp. 210–213. U.S. Pat. No. 4,756,911 describes a membrane controlled delivery system controlling drug release via an insoluble polymer coating which peels off after contact with gastrointestinal fluid. Medicament release is controlled by diffusion or leaching through a gelatinous mass formed on a water-soluble core.

In contrast, a delivery system commonly known as the matrix system typically contains drug uniformly dispersed in cavities within a polymeric matrix. The matrix system is popular for its effectiveness as well as low cost and ease of manufacture. However, the release behavior of these systems is inherently nonlinear in nature as a result of the decreasing release rate with time due to an increase in diffusional resistance and/or a decrease in effective area at the diffusion front.

Numerous matrix systems have been devised in an effort to achieve linear release of the active substance. Several controlled release systems comprising an active substance dispersed in an insoluble matrix encased by an insoluble coating, in which the active agent is exposed through an aperture in the coating, have been described. For example, a ring shaped system in which the aperature is present in the center of the ring is described in EPA 259219. U.S. Pat. No. 3,851,648 discloses a cylindrical device in which the aperature runs along the length of the cylinder and defines a cavity. A truncated cone in which the small end of the cone is exposed to the dissolving fluid is disclosed in EPB-259113. A pharmaceutical tablet having lenticular form is described in European Pat. No. 0 656 204. The basis for these systems is that the surface area of exposed active agent continuously increases as dissolution proceeds, to compensate for the increased diffusion path between the aperature and the dissolving core.

A device comprising a shaped core containing the active substance encased by an impermeable coating which contains one or more apertures, in which the core geometry is used to control the surface area of the exposed surface is disclosed in EPA-542364.

A three-layered matrix system comprising a shaped core coated with erodible polymeric material is disclosed by Cremer et al., *Proceed. Intern. Symp. Control. Rel. Bioact. Mater.*, 1995, 22, 732–733. In this system, the release profile is controlled by erosion rate of the coating layers and the geometrical shape of the core. The delivery systems described in U.S. Pat. No. 3,317,394 and U.S. Pat. No. 5,114,719 achieve controlled dissolution by erosion of soluble material in the coating to form porous channels.

A coated right cylinder having an exposed circumferential strip is disclosed in U.S. Pat. No. 4,972,448.

A polymeric device for extended delivery of small, water-soluble molecules described in U.S. Pat. No. 5,114,719 controls the drug release by a specific manner of loading the biologically active molecules onto the core.

A matrix system for releasing insoluble drugs into the system in granular form comprising a generally cylindrical core which is coated on one or both faces with an inert or insoluble polymeric material is disclosed in U.S. Pat. No. 4,838,177. The core is obtained by compression of the active substance and a swellable and gellable polymer or mixture of polymers. The release profile in this system is controlled by the high degree of swelling of the core.

European Pat. No. 0 598 309 discloses a matrix system wherein the drug-containing matrix comprises swellable, hydrophilic polymers. Similarly, World Pat. No. 94/06416 describes a pharmaceutical tablet capable of liberating one or more drugs at different release rates consisting of erodible matrix layers containing one or more medicaments. Japanese Publication No. 04360826 describes active substance release by a matrix-type medicine-stored interlayer with release-controlling layers predominant in water-soluble polymers. These tablet systems control release by the high degree of swelling and gelling from polymers in the core.

BRIEF DESCRIPTION OF THE DRAWING

FIG. 1 shows, respectively, the structure of a two-layered tablet of type MH when dry, after hydration, and when spent. In tablets of this type, a non-swelling, non-erodible hydrophobic matrix layer M containing an active agent is laminated on a single face with a swellable and gellable hydrophilic barrier layer H. The arrows indicate the directions of drug diffusion. Diffusion occurs through aqueous channels in the unlaminated surfaces of the matrix formed by dissolution of the drug and any soluble excipients and through the hydrophilic barrier layer as it swells and erodes.

FIG. 2 shows, respectively, the structure of a three-layered tablet of type HMH when dry, after hydration, and when spent. In tablets of this type, a non-swelling, non-erodible hydrophobic matrix layer M containing an active agent is laminated on opposing faces with swellable and gellable hydrophilic barrier layers H. The arrows indicate the directions of drug diffusion. Diffusion occurs through the unlaminated sides of the hydrophobic matrix and through the hydrophilic barrier layer as it swells and erodes.

FIG. 3 shows, respectively, the structure of a three-layered tablet of type HML when dry, after hydration, and when spent. In tablets of this type, a non-swelling, non-erodible hydrophobic matrix layer M containing an active agent is laminated on a single face with a swellable and gellable hydrophilic barrier layer H and on the opposite face with a non-swelling, non-erodible hydrophobic barrier layer L. The arrows indicate the directions of drug diffusion. The routes of diffusion are through the unlaminated side wall of the tablet and through the hydrophilic barrier layer as it swells and erodes. Drug diffusion also occurs through the non-swelling, non-erodible barrier layer as soluble ingredients in the layer dissolve and form pores. In systems of this type, the decreasing release rate due to increasing path length from the side wall is compensated by increasing the surface area exposed to the dissolving fluid as the hydrophilic barrier layer swells and erodes.

FIG. 4 shows, respectively, the structure of the two-layered tablet of type ML when dry, after hydration, and when spent. In tablets of this type, a non-swelling, non-erodible hydrophobic matrix layer M containing an active agent is laminated on a single face with a non-swelling, non-erodible hydrophobic barrier layer L. The arrows indicate the directions of drug diffusion. The arrows indicate the directions of drug diffusion. The release mechanism is diffusion through aqueous channels in unlaminated surfaces of the matrix layer formed by dissolution of the drug and any soluble excipients, and through the non-swelling, non-erodible barrier layer as soluble ingredients in the layer dissolve and form pores.

FIG. 5 shows, respectively, the structure of the three-layered tablet of type LML when dry, after hydration, and when spent. In tablets of this type, a non-swelling, non-erodible hydrophobic matrix layer M containing an active agent is laminated on opposing faces with non-swelling, non-erodible hydrophobic barrier layers L. The arrows indicate the directions of drug diffusion. The arrows indicate the directions of drug diffusion. The primary route of diffusion is through the unlaminated side wall of the tablet. Drug diffusion also occurs through the hydrophobic barrier layer as soluble ingredients in the non-swelling, non-erodible barrier layer dissolve and form pores.

SUMMARY OF THE INVENTION

The matrix systems of the present invention utilize one or more barrier layers laminated to a non-erodible matrix containing the active agent to accomplish controlled linear release. Release from laminated surfaces of the modified matrix compensates for a decreasing release rate from the unmodified matrix layer over time. No specialized matrix geometry of the tablet or nonuniform drug loading are necessary to achieve controlled release. Therefore, the matrix systems of the present invention are amenable to production using standard tableting equipment and procedures.

Accordingly, the present invention provides a tablet for the controlled release of an active agent comprising (a) a matrix layer comprising an active agent embedded in a non-swelling, non-erodible hydrophobic matrix; (b) a first barrier layer applied to a single face of the matrix layer; and (c) an optional second barrier layer laminated to the opposite face of the matrix layer; wherein the matrix layer comprises up to about 80% active agent and from about 5% to about 80% by weight of nonswellable waxes or polymeric material insoluble in aqueous medium, and the first and second barrier layers independently comprise (1) polymeric material exhibiting a high degree of swelling and gelling in aqueous medium or (2) nonswellable wax or polymeric material insoluble in aqueous medium.

DETAILED DESCRIPTION OF THE INVENTION

The matrix systems of the present invention provide a layered tablet for substantially linear controlled release of an active agent. A matrix layer of the tablet comprises a non-swelling, non-gelling hydrophobic matrix containing active agent embedded in the matrix. A first and optionally a second barrier layer laminated to a single and opposite face of the matrix layer, respectively, comprise either non-swelling waxes and polymeric material or water-swelling, gellable polymeric material.

Active agent embedded in the non-swelling, non-gelling hydrophobic matrix diffuses through the unprotected sides of the matrix layer. Medicament release from the isolated, unmodified matrix layer of the invention occurs in an inherently nonlinear fashion. Therefore, the first barrier layer and an optional second barrier layer are laminated to the matrix layer to modify nonlinear release from the matrix layer and achieve overall substantially linear release suitable for sustained-release formulations. The active agent embedded in the hydrophobic matrix leaches through channels formed in and between the non-swelling, non-gelling hydrophobic matrix and the barrier layers laminated to each face of the matrix layer. The multilayer tablet of the invention provides a dual advantage in allowing ease of manufacture while affording medicament release in a substantially linear fashion.

In one embodiment, the present invention presents a tablet (MH) comprising a matrix layer comprising an active agent embedded in a non-swelling, non-gelling hydrophobic matrix and a hydrophilic barrier layer laminated to a single face of the matrix layer wherein the matrix comprises up to about 80% active agent and from about 5% to about 80% by weight of nonswellable waxes or polymeric material insoluble in aqueous medium, and the hydrophilic barrier layer comprises polymeric material exhibiting a high degree of swelling and gelling in aqueous medium. The preferred method of applying the hydrophilic barrier layer is compression.

The matrix layer (M) is generally cylindrical in shape having flat, convex, or concave surfaces and comprises active agent uniformly distributed in polymeric material or wax which is non-swelling and non-gelling in aqueous medium and capable of maintaining these characteristics throughout the complete transfer of the active substance.

Polymers suitable for use either alone or in combination in the matrix layer are non-swellable, non-gelling hydrophobic compounds. Suitable hydrophobic compounds typically comprise non-erodible materials selected from acrylates, cellulose, ethylcellulose, cellulose acetate-propionate, polyethylenes, methacrylates, acrylic acid copolymers and high molecular weight polyvinylalcohols. Nonswellable waxes include at least one member selected from the fatty acids or glycerides. A preferred composition of the matrix layer is from about 20% to about 50% active agent, from about 25% to about 50% by weight of polymeric material or wax, and from about 25% to about 50% by weight of pharmaceutically acceptable excipients wherein the weight percentage is based on the total weight of the matrix layer. An especially preferred material for the matrix layer is carnauba wax. The matrix layer is generally prepared by compressing a mixture containing the active substance at a pressure of 4000 to 8000 lbs/cm$^2$ using concave or flat faced punches.

One or more barrier layers having a shape to complement the matrix layer modifies a single and optionally an opposite face of the matrix layer. Composition of the barrier layer depends on the solubility of the medicament embedded in the hydrophobic matrix as well as the amount of medicament loaded onto the matrix. Each barrier layer is independently selected and independently applied to a face of the matrix.

The hydrophilic barrier layer (H) comprises polymeric materials exhibiting a high degree of swelling and gelling in aqueous medium. Polymers having a high degree of swelling suitable for use in the hydrophilic barrier layer are selected from cross-linked sodium carboxymethylcellulose, cross-linked hydroxypropylcellulose, high-molecular weight hydroxypropylmethylcellulose, carboxymethylamide, potassium methacrylatedivinylbenzene copolymer, polymethylmethacrylate, poly (ethyleneoxide), CARBOPOL (high-molecular weight crosslinked acrylic acid homopolymers and copolymers), cross-linked polyvinylpyrrolidone, and high-molecular weight polyvinylalcohols. Swellable polymers are materials that that exhibit the ability to swell in water and retain a significant fraction of water within its structure. See N. A. Peppas and A. R. Khare, "Preparation, Structure and Diffusional Behavior of Hydrogels in Controlled Release", *Advanced Drug Delivery Reviews,* 1993, 11, 1–35. Other materials suitable for use in the hydrophilic barrier layer include xanthum gum and alginate.

Gellable polymers suitable for use in the hydrophilic barrier layer are selected from polyethylenedioxide, methylcellulose, carboxymethylcellulose, low molecular weight hydroxypropylmethylcellulose, low molecular weight polyvinyl alcohols, polyoxyethyleneglycols and non-crosslinked polyvinylpyrrolidone.

Polymers simultaneously exhibiting swelling and gelling properties suitable for use in the hydrophilic barrier layer are selected from medium viscosity high-molecular weight hydroxypropylmethylcellulose and medium viscosity polyvinyl alcohols.

A preferred composition of the hydrophilic barrier layer comprises from about 5% to about 80% by weight of a polymeric material exhibiting a high degree of swelling in aqueous medium, and from about 90% to about 10% by weight of a polymeric material exhibiting a high degree of gelling in aqueous medium, or from about 40% to about 80% by weight of a single polymer which exhibits both swelling and gelling in aqueous medium, and from about 20% to about 60% by weight of pharmaceutically acceptable excipients wherein the weight percentage is based on the total weight of the barrier layer. The more preferred composition of the hydrophilic barrier layer is from about 40% to about 80% by weight of a single polymer which exhibits both swelling and gelling in aqueous medium, and from about 20% to about 60% by weight of pharmaceutically acceptable excipients. The preferred polymer for use in the hydrophilic barrier layer is medium viscosity high-molecular weight hydroxypropylmethylcellulose.

The hydrophobic barrier layer (L) provides a non-swelling, non-erodible barrier layer for modifying release from the unmodified core. The hydrophobic barrier layer comprises nonswellable wax or polymeric insoluble material in aqueous medium. Polymeric material suitable for the hydrophobic barrier layer is selected from the group consisting of acrylates, cellulose, ethylcellulose, cellulose acetate-propionate, polyethylenes, methacrylates, acrylic acid copolymers and high molecular weight polyvinylalcohols, and the waxes include at least one member selected from the fatty acids or glycerides.

A preferred composition of the hydrophobic barrier layer is from about 10% to about 90% by weight of nonswellable waxes or polymeric material insoluble in aqueous medium and from about 90% to about 10% by weight of pharmaceutically acceptable excipients. The most preferred material for the hydrophobic barrier is a nonswellable wax selected from the fatty acids or glycerides. The most preferred wax for use in the hydrophobic barrier layer is carnauba wax.

The hydrophilic and/or hydrophobic barrier layers are typically applied to the matrix layer by laminating the barrier layer to one or both faces of the hydrophobic matrix layer. Preferably, lamination of the barrier layer is accomplished by compressing the barrier layer and the matrix leaving the edge of the core exposed. Layered matrix tablets can be prepared using concave or flat-faced punches by compressing a mixture containing the compounds for the barrier layer or the matrix layer to be prepared at 200–400 lbs/cm$^2$. Additional layers are compressed to the concave or flat-face punch by the same method varying the mixture in accordance with the composition of each desired layer. From about 4000 lbs/cm$^2$ to 8000 lbs/cm$^2$ pressure is preferred for compressing the finished tablet.

Pharmaceutically acceptable excipients or carriers suitable for use in the matrix and barrier layer include sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Under the action of digestive juices, embedded medicament releases from the center of the non-soluble, non-gelling matrix into the surrounding digestive fluids. Dissolution of the medicament release from the unlaminated sides and the laminated and optionally laminated face of the multilayer tablet. An embedded medicament leaches through channels formed in and between the non-swelling, non-gelling hydrophobic matrix and the barrier layers laminated to each face of the matrix layer. The polymeric material of the hydrophilic layer exhibiting a high degree of swelling in aqueous medium delays medicament release from the laminated surface of the matrix layer by retarding movement of the medicament from the matrix into the outer fluids.

Release is delayed as the medicament moves into the swelling, gelling material of the hydrophilic matrix and dissolves as the hydrophilic layer dissolves.

Alternately, or on the opposite face, the hydrophobic barrier layer comprising 10% to about 90% by weight of nonswellable waxes or polymeric material insoluble in aqueous medium slows medicament release from the face to which it is laminated. Medicament moves through the insoluble core in a manner similar to the channels formed in the non-swelling, non-gelling matrix. Drug diffusion paths of each embodiment of the invention are illustrated in FIGS. 1–5.

Figure 1:
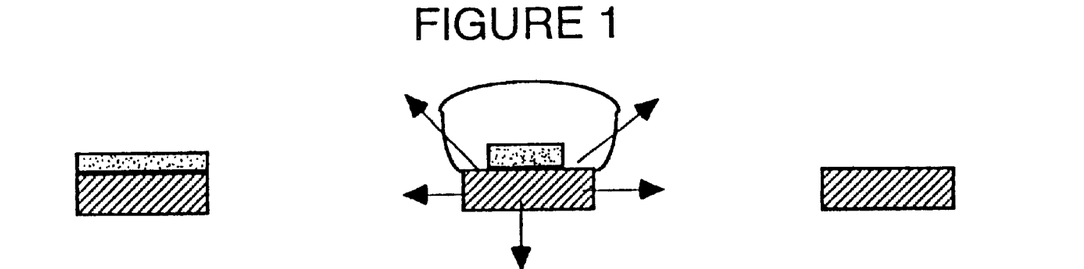
Figure 2:
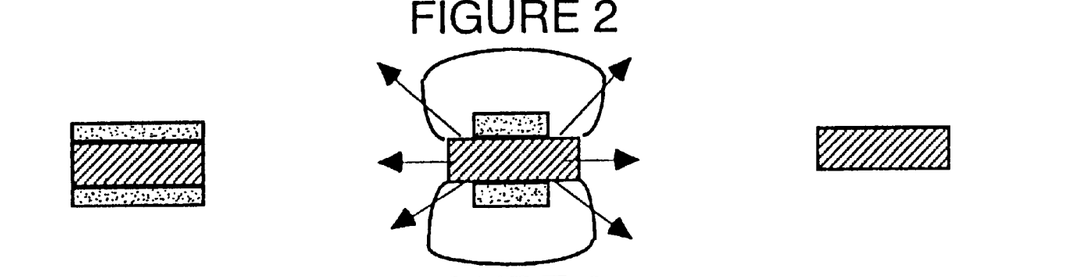
Figure 3:
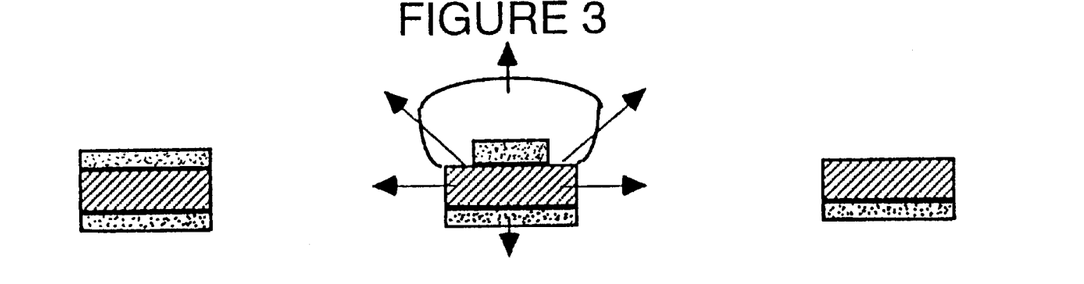
Figure 4:
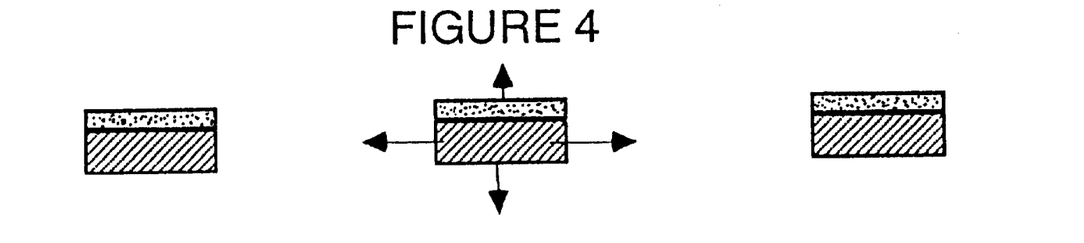
Figure 5:
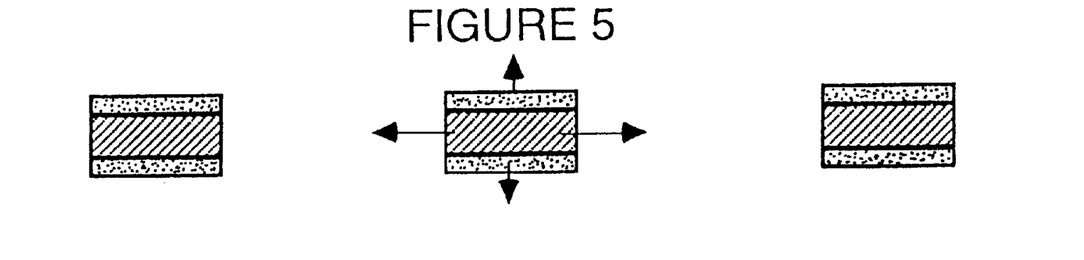
Figure 6:
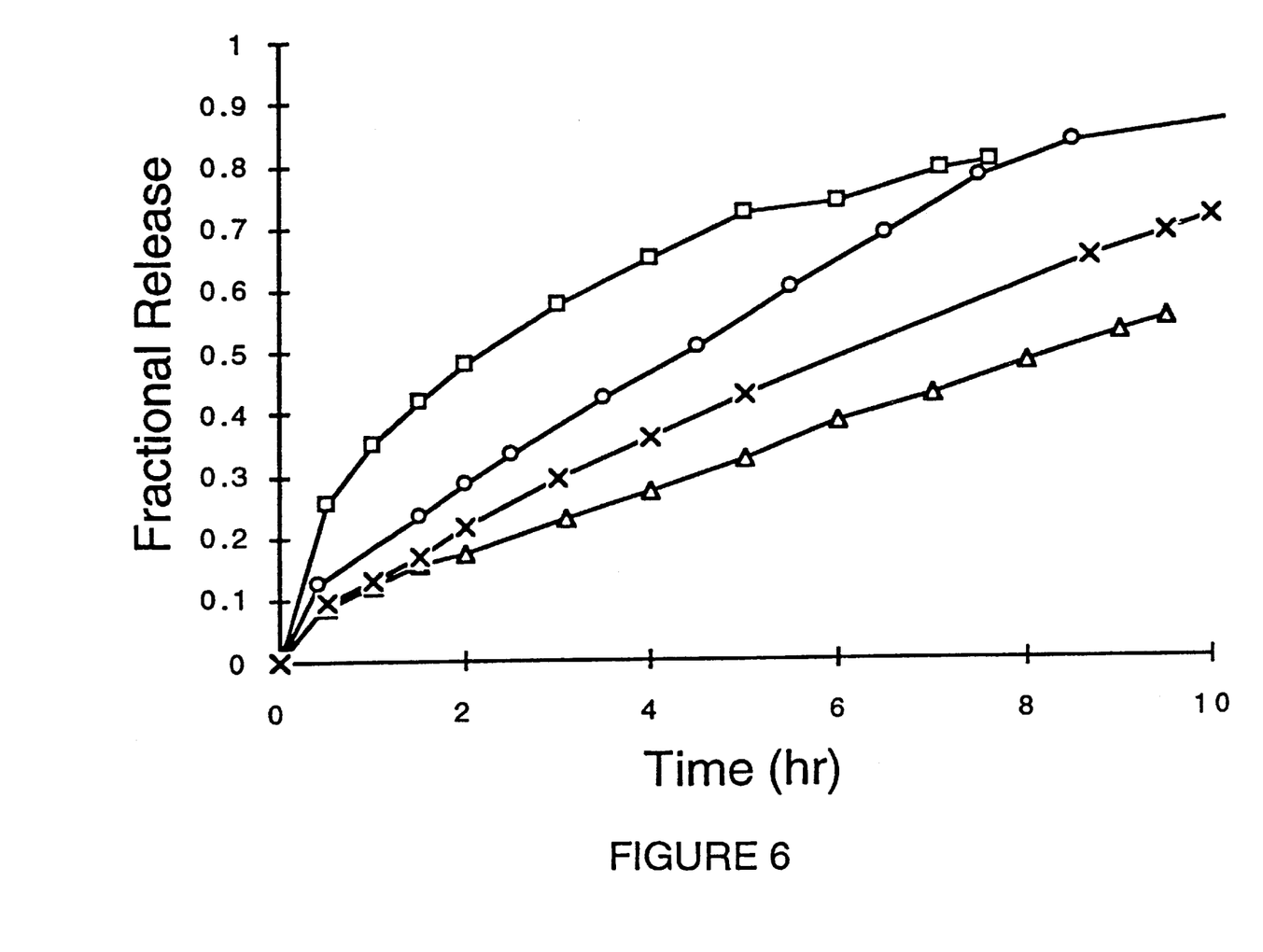
FIG. 6 is a plot of the fractional release in vitro of pseudoephedrine vs. time in hours for representative matrix formulations. The squares represent unmodified matrix tablet A. The circles represent a three-layed tablet of type HMH (formulation G). The triangles represent a three-layered tablet of type LML (formulation J). A three-layered tablet of type HML (formulation N) is represented by the symbol "x".
Figure 7:
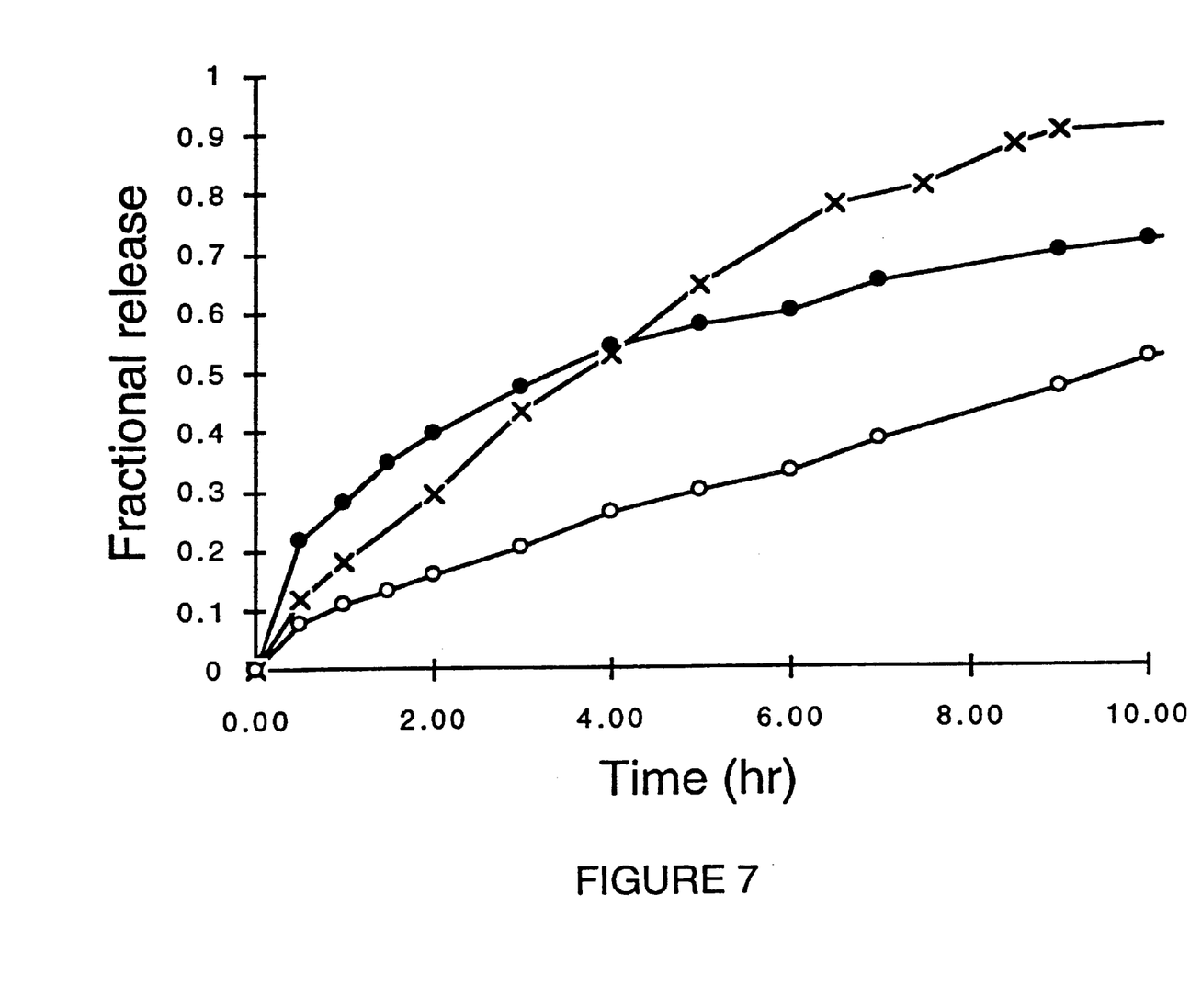
FIG. 7 is a plot of the fractional release in vitro of aminophylline or 2-methyl-3-(2-(S)-pyrroldinylmethoxy) pyridine vs. time in hours for a three-layer tablet of type HML. The open circles represent formulation Q. Unmodified matrix formulation C is represented by the filled in circles.

Drug release profiles describing the amount of drug release relative to time in the present invention represent medicament release at a nearly constant rate. As illustrated in FIGS. 6 and 7, the multilayered embodiments of the invention have been modified to achieve substantially linear (or zero-order) release. A curved portion respectively representing drug release of the matrix layer alone contrasts with the statistically demonstrated linearity of prepared multilayer systems in each profile. FIG. 6 illustrates drug release in the unmodified matrix relative to the HMH, LML, and HML tablet types. FIG. 7 compares the fractional release of the unmodified matrix against an HML tablet type containing aminophylline active medicament. Regression data in Table 6 and 7 below summarize the statistical support for linear release of the medicament. Additional support for the zero-order sustained release of the matrix tablet can be found in the articles, *J. of Controlled Release* 51:123–130 (1998) and *J. of Controlled Release* 52:149–158(1998).

In another embodiment, the present invention provides a tablet (ML) comprising a matrix layer as described above and a hydrophobic barrier layer applied to the matrix layer wherein the matrix layer comprises from about 20% to about 50% active agent, from about 25% to about 50% by weight of carnauba wax, and from about 25% to about 50% by weight of pharmaceutically acceptable excipients wherein the weight percentage is based on the total weight of the matrix layer, and the barrier layer comprises from about 10% to about 90% by weight of carnauba wax and from about 90% to about 10% by weight of pharmaceutically acceptable excipients. The barrier layer is preferably applied to a face of the matrix layer by compression.

In another embodiment, the present invention provides a three-layered tablet (HMH) in which hydrophilic barrier layers, which may be the same or different, are applied to opposite faces of the matrix layer. Three-layer matrix tablets are preferably prepared by compression as generally described above using concave or flat-faced punches. The ingredients for the bottom layer barrier layer are placed in the die and compressed at from about 200 to about 400 lbs/cm$^2$. The ingredients for the matrix layer are then added and recompressed at from about 200 to about 400 lbs/cm$^2$. The ingredients for the top layer are then added and the entire assemblage is compressed at from about 4000 to about 8000 lbs/cm$^2$.

In a preferred three-layer tablet of type HMH, the matrix layer comprises from about 20% to about 50% active agent, from about 25% to about 50% by weight of carnauba wax, and from about 25% to about 50% by weight of pharmaceutically acceptable excipients wherein the weight percentage is based on the total weight of the matrix layer, and the first and second barrier layers independently comprise from about 40% to about 80% by weight of medium-viscosity hydroxypropylmethylcellulose and from about 20% to about 60% by weight of pharmaceutically acceptable excipients wherein the weight percentage is based on the total weight of the barrier layer.

In another embodiment, the present invention provides a three-layered tablet (LML) in which hydrophobic barrier layers, which may be the same or different, are applied to opposite faces of the matrix layer. In a preferred three-layer tablet of type LML, the matrix layer comprises from about 20% to about 50% active agent, from about 25% to about 50% by weight of carnauba wax, and from about 25% to about 50% by weight of pharmaceutically acceptable excipients wherein the weight percentage is based on the total weight of the matrix layer, and the first and second barrier layers independently comprise from about 10% to about 90% by weight of carnauba wax and from about 90% to about 10% by weight of pharmaceutically acceptable excipients.

In another embodiment, the present invention provides a three-layered tablet (HML) in which the matrix layer is laminated on one face with hydrophilic barrier layer, and on the opposite face with a lipohilic barrier layer. In a preferred three-layer tablet of type HML, the matrix layer comprises from about 20% to about 50% active agent, from about 25% to about 50% by weight of carnauba wax, and from about 25% to about 50% by weight of pharmaceutically acceptable excipients wherein the weight percentage is based on the total weight of the matrix layer; the hydrophilic barrier layer comprises from about 5% to about 80% by weight of medium-viscosity hydroxypropylmethylcellulose and from about 20% to about 60% by weight of pharmaceutically acceptable excipients wherein the weight percentage is based on the total weight of the barrier layer; and the hydrophobic barrier layer comprises from about 30% to about 90% by weight of carnauba wax and from about 70% to about 10% by weight of pharmaceutically acceptable excipients.

The active agents of the present invention may be any material suitable for release into aqueous medium including pharmaceutical agents, insecticides, pesticides, perfumes, and water-treatment agents such as germicides. Preferred active agents are pharmaceutical agents.

Representative pharmaceutical agents suitable for use in the tablets of the present invention include a variety of inorganic and organic pharmaceutical agents such as cognition enhancers, analgesics, anorexics, antihelmintics, antibacterials, anticonvulsants, antifungals, antidepressants, antibiotics, antihistamines, antiulcer drugs, antihypertensives, bronchodilators, immunosuppressants, aldose reductase inhibitors, blood glucose lowering agents, adrenergics, muscle relaxants, anti-Parkinson agents, muscle contractants, hormonal agents, contraceptives, diuretics, electrolytes, bronchodilators, hypnotics, steroids, serotonin agonists or antagonists and $H_2$ antagonists.

Bronchodilators such as aminophylline are preferred pharmaceutical agents.

Also preferred are cough or cold agents such as brompheniramine dexbrompheniramine and chlorpheniramine maleates, phenylepherine and pseudoephedrine hydrochlorides and cetirizine.

Cognition enhancers, as described in U.S. Ser. No. 129, 223, are a particularly preferred class of active agents.

The most preferred agent for use in the tablets of the present invention is 2-methyl-3-(2-(S)-pyrroldinylmethoxy)pyridine.

The matrix type (MH, ML, LML, HMH, or HML) suitable for delivery of a given drug is selected based on (1) the solubility of the drug and (2) drug loading in the matrix layer. For purposes of making this selection, drugs may be classified by solubility as follows:

| (i) | "very soluble" | (>1 g/mL); |
|---|---|---|
| (ii) | "freely soluble" | (>0.1 g/mL and <1 g/mL); |
| (iii) | "soluble" | (>0.033 g/mL and <0.1 g/mL); |
| (iv) | "sparingly soluble" | (>0.01 g/mL and <0.033 g/mL); |
| (v) | "slightly soluble" | (>0.001 g/mL and <0.01 g/mL); and |
| (vi) | "very slightly soluble" | (>0.0001 g/mL and <0.001 g/mL). |

In general, two layered tablets of type MH and ML are preferred for drugs in solubility classes (v) and (vi) and drug loading of <30%.

All five matrix types (MH, ML, LML, HMH, or HML) are suitable to control the release of drugs in categories (i) to (v).

Three-layered tablets (HMH, LML and HML) are suitable for drugs in categories (i) to (v) with drug loading up to 60%. However, for drugs in categories (iv) and (v) with drug loading of greater than 30%, tablets of type HML or HMH are preferred over tablets of type LML.

The release profile of an active agent from the matrix systems of the present invention is controlled by a number of variables including the thickness of the barrier layer(s), the concentration of soluble or insoluble material (polymer or wax) in the matrix and barrier layer(s), and the amount of any soluble or insoluble excipients.

For tablets of type MH and HMH, linearity of release can be improved by using a higher amount of barrier layer, or higher viscosity hydroxypropylmethylcellulose. Linearity of release is maintained by partial substitution with soluble excipients such as lactose or insoluble excipients such as Avicel PH101 (microcrystalline cellulose, swellable) or dicalcium phosphate (nonswellable), or mixtures thereof, does not result in nonlinearity.

For tablets of type ML and LML, the factor exerting the greatest influence on release kinetics is the wax concentration in the barrier layers. In general, increasing the wax concentration results in increased time dependency of release.

In three-layered tablets of type HML, linearity of release is generally increased by using a smaller hydrophobic barrier layer relative to the hydrophilic barrier layer.

For all systems, the presence of high concentrations of diffusion-limiting materials (insoluble polymers and waxes) and insoluble excipients such as dicalcium phosphate and microcrystalline cellulose (Avicel, FMC Corp.) in either the barrier or matrix layer result in a slower release rate.

The foregoing may be better understood by reference to the following examples, which are presented for illustration and are not intended to limit the scope of the invention as defined in the appended claims.

EXAMPLE 1

Preparation of Single Layer Hydrophobic Matrix (M)

Drug and excipients were slowly added to molten wax and mixed well by stirring. The mixture was allowed to cool to ambient temperature while maintaining mixing. The congealed solids were milled and passed through a 850 micron (20 mesh) screen to obtain granules. The tablets were prepared by compressing at 4000–8000 lbs/cm$^2$ using a flat-faced punch.

Using the foregoing procedure, 250 mg single layer hydrophobic matrix tablets having the following composition were prepared.

TABLE 1

Composition of Single Layer Hydrophobic Matrix Tablets

| Formulation | A | B | C |
|---|---|---|---|
| Pseudoephidrine | 24% | — | — |
| [2-methyl-3-(2-(S)-pyrroldinylmethoxy)pyridine] | — | 13.8% | — |
| Aminophylline | — | — | 41% |
| Carnauba wax | 50% | 60% | 35% |
| Lactose (anhydrous) | 26% | 26.2% | 24% |
| Total | 250 mg | 250 mg | 250 mg |

EXAMPLE 2

Preparation of Layered Matrix MH

Tablets comprising a hydrophobic matrix (M) and a hydrophilic barrier layer (H) were prepared as follows. Drug and excipients were slowly added to molten wax and mixed well by stirring. The mixture was allowed to cool to ambient temperature while maintaining mixing. The congealed solids were milled and passed through a 850 micron (20 mesh) screen to obtain granules. Polymer and excipients were dry mixed and used as is. The barrier layer and matrix layer were compressed in succession using concave or flat-faced punches to form two-layered tablets. The initial compression force was 200–400 lbs/cm$^2$. The final compression force was 5400 lbs/cm$^2$.

Using the foregoing procedure, a two-layered matrix tablet having the following composition was prepared.

TABLE 2

Composition of Two-Layer Matrix Tablet MH

| | Formulation D | |
|---|---|---|
| | M | H |
| Psuedoephidrine | 24% | — |
| Carnauba wax | 50% | — |
| Methocell K100M | — | 80% |
| Lactose (anhydrous) | 26% | 20% |
| Total | 250 mg | 100 mg |

EXAMPLE 3

Preparation of Layered Matrix HMH

Three-layer tablets comprising a hydrophilic barrier layer (H), a hydrophobic matrix (M) and a hydrophilic barrier layer (H) were prepared as follows. Psuedoephedrine and lactose (anhydrous) were slowly added to molten carnauba wax and mixed well by stirring. The mixture was allowed to cool to ambient temperature while maintaining mixing. The congealed solids were milled and passed through a 850 micron (20 mesh) screen to obtain granules. Polymer and excipients were dry mixed and used as is. Three-layer matrix tablets were prepared by compressing the bottom barrier layer at 200–400 lbs/cm$^2$ followed by the matrix layer 200–400 lbs/cm$^2$ and the top barrier layer at 4500 lbs/cm$^2$.

Using the foregoing procedure, three-layered matrix tablets having the compositions described in Table 4 were prepared.

TABLE 3

Composition of Three-Layer Matrix Tablets HMH

| | Formulation | | | |
|---|---|---|---|---|
| | E | | F | |
| | M | H | M | H |
| Psuedoephidrine | 24% | — | 24% | — |
| Carnauba wax | 50% | — | 50% | — |
| Methocell K100M | — | 80% | 26% | 50% |
| Lactose (anhydrous) | 26% | 20% | — | 30% |
| Avicell PH101 | — | — | — | 20% |
| dicalcium phosphate | — | — | — | — |
| Total | 250 mg | 100 mg | 250 mg | 100 mg |

| | Formulation | | | |
|---|---|---|---|---|
| | G | | H | |
| | M | H | M | H |
| Psuedoephidrine | 24% | — | 24% | — |
| Carnauba wax | 50% | — | 50% | — |
| Methocell K100M | — | 40% | — | 50% |
| Lactose (anhydrous) | 26% | 60% | 26% | 30% |
| Avicell PH101 | — | — | — | — |
| dicalcium phosphate | — | — | — | 20% |
| Total | 250 mg | 100 mg | 250 mg | 100 mg |

| | Formulation I | |
|---|---|---|
| | M | H |
| Psuedoephidrine | 24% | — |
| Carnauba wax | 50% | — |
| Methocell K100M | — | 50% |
| Lactose (anhydrous) | 26% | 30% |
| Avicell PH101 | — | 10% |
| dicalcium phosphate | — | 10% |
| Total | 250 mg | 100 mg |

EXAMPLE 4

Preparation of Layered Matrix LML

Three-layer tablets comprising a hydrophobic barrier layer (L), a hydrophobic matrix (M) and a hydrophobic barrier layer (L) were prepared as follows. Drug and excipients were slowly added to molten carnauba wax and mixed well by stirring. The mixture was allowed to cool to ambient temperature while maintaining mixing. The congealed solids were milled and passed through a 850 micron (20 mesh) screen to obtain granules. The barrier layers were prepared by adding lactose to carnauba wax at 90° C. and mixing thoroughly. The mixture was allowed to cool to ambient temperature while maintaining mixing. The resultant mass was milled and passed through a 850 micron (20 mesh) screen to obtain granules. Three-layer matrix tablets were prepared using concave or flat-faced punches by compressing the bottom barrier layer at 200–400 lbs/cm$^2$ followed by the matrix layer 200–400 lbs/cm$^2$ and the top barrier layer at 4500 lbs/cm$^2$.

Using the foregoing procedure, three-layered matrix tablet having the following compositions were prepared.

TABLE 4

Composition of Three-Layer Matrix Tablets LML

| | Formulation J | | |
|---|---|---|---|
| | M | L1 | L2 |
| Psuedoephidrine | 24% | — | — |
| Carnauba wax | 50% | 30% | 10% |
| Lactose (anhydrous) | 26% | 70% | 90% |
| dicalcium phosphate | — | — | — |
| Total | 250 mg | 150 mg | 100 mg |

TABLE 4

| Formulation | M | L1 | L2 |
|---|---|---|---|
| | K | | |

| | | | |
|---|---|---|---|
| | 26.8% | — | — |
| Carnauba wax | 33.7% | 50% | 50% |
| Lactose (anhydrous) | 32.7% | 50% | 50% |
| dicalcium phosphate | 6.8% | — | — |
| Total | 148.4 mg | 100 mg | 100 mg |
| | | L | |

| | | | |
|---|---|---|---|
| | 27.3% | — | — |
| Carnauba wax | 33.3% | 50% | 50% |
| Lactose (anhydrous) | 39.4% | 50% | 50% |
| dicalcium phosphate | — | — | — |
| Total | 150 mg | 100 mg | 100 mg |
| | | M | |

| | | | |
|---|---|---|---|
| | 27.6% | — | — |
| Carnauba wax | 40% | 50% | 50% |
| Lactose (anhydrous) | — | 25% | 25% |
| dicalcium phosphate | 32.4% | 25% | 25% |
| Total | 148.4 mg | 100 mg | 100 mg |

EXAMPLE 5

Preparation of Layered Matrix HML

Three-layer tablets comprising a hydrophilic barrier layer (H), a hydrophobic matrix (M) and a hydrophobic barrier layer (L) were prepared as follows. Drug and excipients were slowly added to molten carnauba wax and mixed well by stirring. The mixture was allowed to cool to ambient temperature while maintaining mixing. The congealed solids were milled and passed through a 850 micron (20 mesh) screen to obtain granules. The hydrophilic barrier layer H was prepared by dry-mixing the polymer and excipients. The hydrophobic barrier layer L was prepared by adding lactose to carnauba wax at 90° C. and mixing thoroughly. The mixture was allowed to cool to ambient temperature while maintaining mixing. The resultant mass was milled and passed through a 850 micron (20 mesh) screen to obtain granules. Three-layer matrix tablets were prepared using concave or flat-faced punches by compressing the bottom barrier layer at 200–400 lbs/cm² followed by the matrix layer at 200–400 lbs/cm² and the top barrier layer at 4500 lbs/cm².

Using the foregoing procedure, three-layered matrix tablet having the following compositions were prepared.

TABLE 5

Composition of Three-Layer Matrix Tablets HML

| Formulation | M | H | L |
|---|---|---|---|
| | | N | |
| Pseudoephidrine | 24% | — | — |
| Carnauba wax | 50% | — | 30% |
| Methocell K15M | — | 80% | — |
| Lactose (anhydrous) | 26% | 20% | 70% |
| dicalcium phosphate | — | — | — |
| Total | 250 mg | 150 mg | 200 mg |
| | | O | |
| | 26.8% | — | — |

| Carnauba wax | 33.7% | — | 90% |
| Methocell K00MP CR | — | 70% | 10% |
| Lactose (anhydrous) | 32.7% | 15% | — |
| dicalcium phosphate | 6.8 | — | — |
| Avicel PH101 | — | 15% | — |
| Total | 100 mg | 100 mg | 100 mg |
| | | P | |
| Aminophyline | 41% | — | — |
| Carnauba wax | 35% | — | 30% |
| Methocell K15M | — | 80% | — |
| Lactose (anhydrous) | 24% | 20% | 70% |
| Total | 250 mg | 150 mg | 200 mg |
| | | Q | |
| Aminophyline | 41% | — | — |
| Carnauba wax | 35% | — | 30% |
| Methocell K15M | — | 80% | — |
| Lactose (anhydrous) | 24% | 20% | 70% |
| Total | 250 mg | 100 mg | 100 mg |

EXAMPLE 6

In Vitro Release Rates of Matrix Tablets

The in vitro release rates of matrix tablets were determined using USP apparatus II. The test conditions were as follows:

| Method | Paddle |
|---|---|
| Medium | Distilled Water |
| Volume of medium | 900 mL |
| Temperature | 37° C. |
| Speed | 100 rpm |
| Sampling volume | 3 mL |
| Sampling Interval | 0, 0.5, 1, 2, 3, 4, 5, 6, 7, 8, 9 and 24 hours |

At each sampling interval, 3 mL samples were taken and replaced with the same volume of distilled water to maintain a constant volume. Concentrations of the test compounds in the samples were assayed by UV spectrometry at 258 nm for pseudoephedrine, 290 nm for theophylline and 276 nm for 2-methyl-3-(2-(S)-pyrrolidinylmethyloxy)pyridine, respectively. Cumulative amounts of drug released from the tablets were calculated and plotted as a function of time. The release rates for matrix tablets G, J and M and single layer tablet A are summarized in FIG. 6. Results of the study were statistically analyzed to determine the fit to the zero-order linear equation shown below, $$F = kt + \beta_0$$

wherein k is the slope and $\beta_0$ is the intercept. Summary and fitting data tabulated in Table 6 demonstrates greater than or equal to 0.996 correlation for the HMH, HML, and LML matrix systems of the invention, which indicates a very good fit to the standard linear equation. The unmodified matrix (M), showing 0.9360 correlation (not a good fit) to the standard linear equation, exhibits good fit to a standard nonlinear equation. The statistical analysis demonstrates that a single matrix layer (M) can be modified to release an active agent in a substantially linear fashion by forming a multilayer tablet from the single layer tablet and one or more barrier layers laminated to the matrix.

TABLE 6

Summary of Fitting to Linear Equation (FIG. 6)

| System | Slope | Intercept | $R^2$ of Linear Fit |
|---|---|---|---|
| M | 0.0727 | 0.3035 | 0.9360 |
| HMH | 0.0911 | 0.0976 | 0.9993 |
| HML | 0.0646 | 0.0815 | 0.9956 |
| LML | 0.0506 | 0.0731 | 0.9989 |

The results for matrix tablet Q and single layer tablet C are summarized in FIG. 7. Regression data illustrates that linear release of the medicament can be achieved in a matrix tablet having aminophyline as the medicament.

TABLE 7

Summary of Fitting to Linear Equation (FIG. 7)

| System | Slope | Intercept | $R^2$ of Linear Fit |
|---|---|---|---|
| M | 0.050 | 0.277 | 0.9176 |
| Aminophyline | 0.045 | 0.067 | 0.9977 |

As indicated in FIGS. 6 and 7 and the related summary data, substantial linearity of drug release can be obtained from all three tablet designs, i.e. HMH, LML and HML.

EXAMPLE 7

In Vivo Performance of Layered Matrix HML

The in vivo performance of the three-layered matrix tablet Q was compared to the single layer matrix tablet C in beagle dogs.

Figure 8:
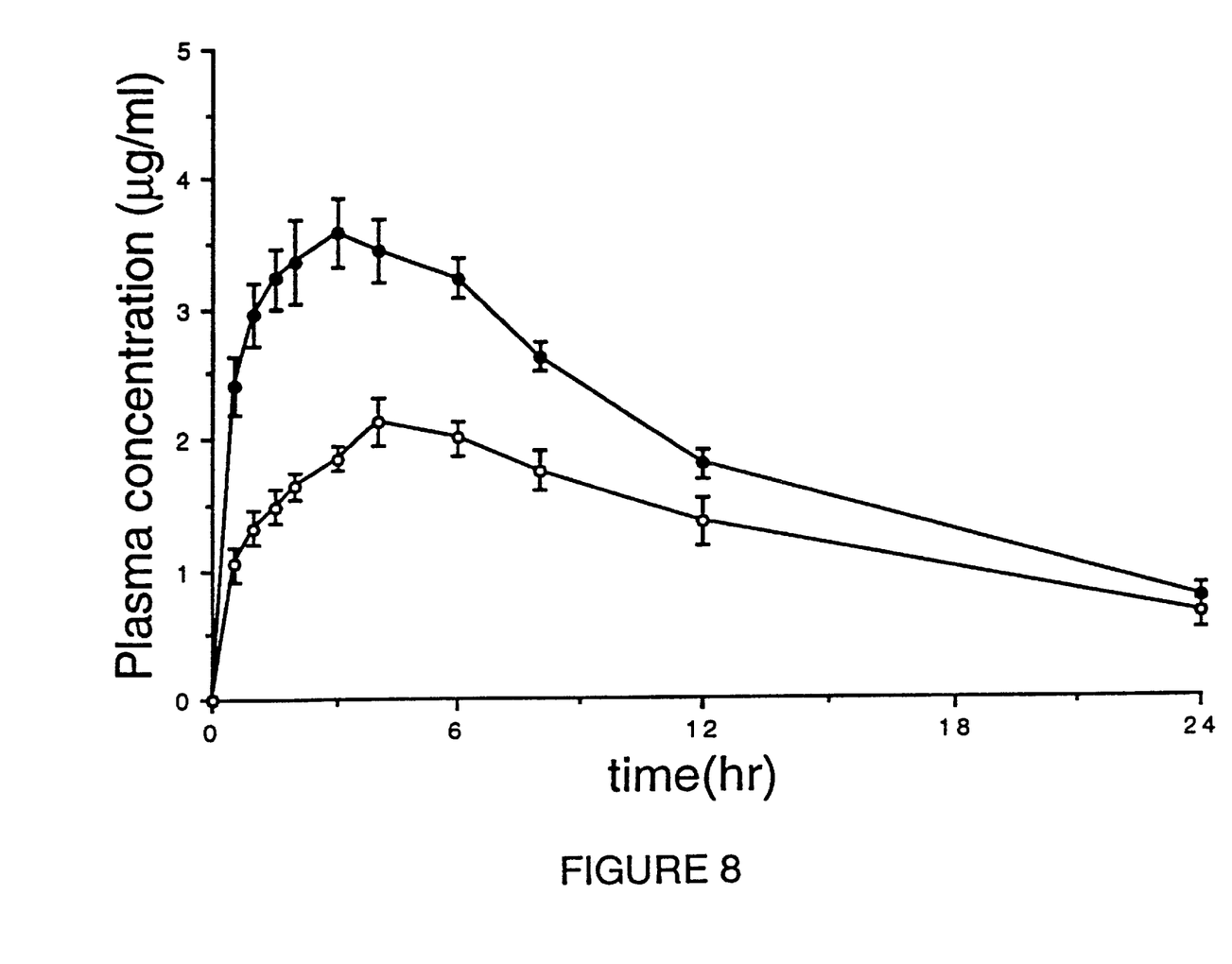
FIG. 8 is a plot of the plasma level in $\mu$g/mL vs. time in hours of aminophylline following oral administration to beagle dogs of the unmodified matrix formulation C and a three-layered matrix tablet of type HML (formulation Q). The upper curve represents formulation C and the lower curve represents formulation Q.

Nine beagle dogs weighing 9.3–14.2 kg were used for the study. All dogs were fasted overnight before dosing. A single dose three-way crossover design with a 1 week dosing interval was used. The reference formulation was an aqueous solution on aminophylline (10.2 mg/mL). Drug was orally administered (102 mg) followed by 100 mL of water. Food was returned to the dogs after the 6-hour blood sample was obtained. Serial blood samples were collected at 0, 0.25, 0.5, 1, 1.5, 2, 3, 4, 6, 8, 12, 24, and 32 hours after dosing. Plasma samples were immediately separated from the blood and frozen at −20° C. until assayed by TDX fluorescence polarization immunoassays. The results are summarized in FIG. 8. As indicated in FIG. 8, prolonged absorption was attained from both tablets. The more rapid early absorption rate observed for the single-layer tablet can be attributed to higher initial release due to nonlinear release as well as the overall higher release rate when compared to the three-layered tablet.

EXAMPLE 8

In Vivo Performance of Layered Matrix LML

Figure 9:
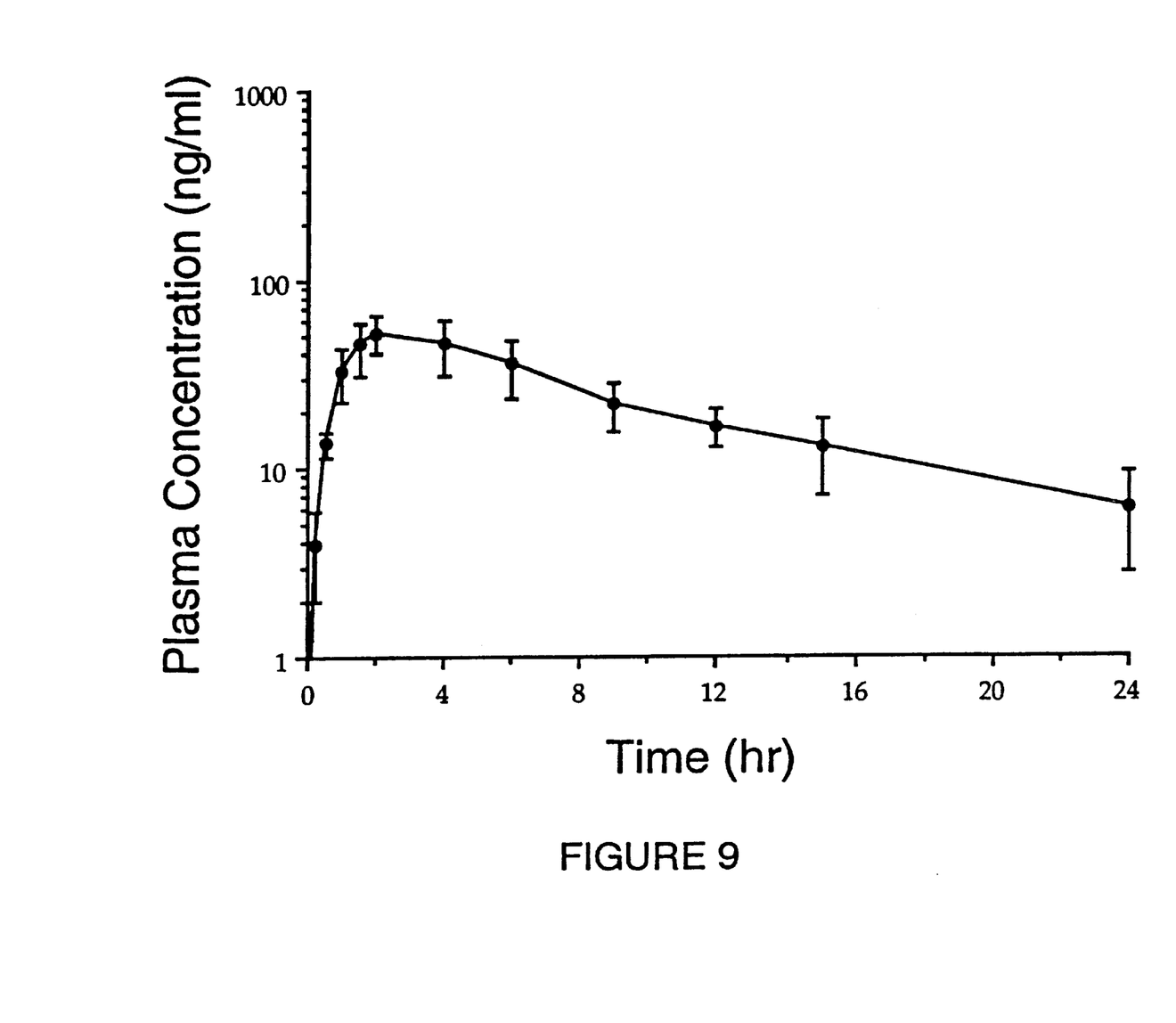
FIG. 9 is a plot of the plasma level in ng/mL vs. time in hours of 2-methyl-3-(2-(S)-pyrrolidinylmethoxy)pyridine following oral administration to beagle dogs of a three-layered matrix table of type LML (formulation K).

The in vivo performance of the three-layered matrix tablet K in beagle dogs was measured as described in Example 7. The results are summarized in FIG. 9. As indicated in FIG. 9, prolonged release is also attained using matrix tablets of type LML.

What is claimed is:

1. A tablet for the controlled release of an active agent comprising
   (a) a matrix layer comprising an active agent embedded in a non-swelling, non-gelling hydrophobic matrix;
   (b) a first barrier layer laminated to a single face of the matrix layer; and
   (c) an optional second barrier layer laminated to the opposite face of the matrix layer;
   wherein the matrix layer comprises up to about 80% active agent and from about 5% to about 80% by weight of nonswellable waxes or polymeric material insoluble in aqueous medium, and the first and second barrier layers independently comprise
      (1) polymeric material exhibiting a high degree of swelling and gelling in aqueous medium or
      (2) nonswellable wax or polymeric material insoluble in aqueous medium.

2. The tablet according to claim 1, wherein the matrix layer comprises from about 20% to about 50% active agent, from about 25% to about 50% by weight of nonswellable wax, and from about 25% to about 50% by weight of pharmaceutically acceptable excipients wherein the weight percentage is based on the total weight of the matrix layer.

3. The tablet according to claim 2, wherein the nonswellable wax is carnauba wax.

4. The tablet according to claim 1, wherein the polymeric material having a high degree of swelling in aqueous medium is selected from the group consisting of cross-linked sodium carboxymethylcellulose, cross-linked hydroxypropylcellulose, high-molecular weight hydroxypropylmethylcellulose, carboxymethylamide, potassium methacrylatedivinylbenzene copolymer, polymethylmethacrylate, poly(ethyleneoxide), cross-linked polyvinylpyrrolidone, high-molecular weight polyvinylalcohols, high-molecular weight crosslinked acrylic acid homopolymers and copolymers xanthum gum and alginate; and
   the polymeric material having a high degree of gelling is selected from the group consisting of polyethylenedioxide, methylcellulose, carboxymethylcellulose, low molecular weight hydroxypropylmethylcellulose, low molecular weight polyvinyl alcohols, polyoxyethyleneglycols and non-crosslinked polyvinylpyrrolidone.

5. The tablet according to claim 4, wherein the barrier layer comprises from about 5% to about 80% by weight of a polymeric material exhibiting a high degree of swelling in aqueous medium, and from about 90% to about 10% by weight of a polymeric material exhibiting a high degree of gelling in aqueous medium and from about 20% to about 60% by weight of pharmaceutically acceptable excipients wherein the weight percentage is based on the total weight of the barrier layer.

6. The tablet according to claim 5 wherein the barrier layer comprises from about 40% to about 80% by weight of a single polymer which exhibits both swelling and gelling in aqueous medium, and from about 20% to about 60% by weight of pharmaceutically acceptable excipients wherein the weight percentages are based on the total weight of the barrier layer.

7. The tablet according to claim 6 wherein the polymer which exhibits both swelling and gelling in aqueous medium is selected from medium-viscosity polyvinylalcohols and medium-viscosity hydroxypropylmethylcellulose.

8. The tablet according to claim 7 wherein the polymer which exhibits both swelling and gelling in aqueous medium is medium-viscosity hydroxypropylmethylcellulose.

9. The tablet according to claim 1, wherein the barrier layer comprises from about 30% to about 90% by weight of nonswellable waxes or polymeric material insoluble in aqueous medium and from about 70% to about 10% by weight of pharmaceutically acceptable excipients, wherein the polymeric material is selected from the group consisting of acrylates, cellulose, ethylcellulose, cellulose acetate-propionate, polyethylenes, methacrylates, acrylic acid copolymers and high molecular weight polyvinylalcohols, and the waxes include at least one member selected from the fatty acids or glycerides.

10. The tablet according to claim 9, wherein the barrier layer comprises from about 30% to about 90% by weight of nonswellable wax selected from the fatty acids or glycerides.

11. The tablet according to claim 1, wherein the barrier is laminated to the matrix layer by compression.

12. The tablet according to claim 1, comprising the matrix layer and the first barrier layer laminated to the matrix layer, wherein the barrier layer is selected from polymeric materials exhibiting a high degree of swelling and gelling in aqueous medium.

13. The tablet according to claim 1, comprising the matrix layer and the first barrier layer laminated to the matrix layer, wherein the barrier layer is selected from nonswellable wax or polymeric material insoluble in aqueous medium.

14. The tablet according to claim 12, further comprising the second barrier layer laminated to the opposite face of the matrix layer, wherein the second barrier layer is selected from polymeric materials exhibiting a high degree of swelling and gelling in aqueous medium.

15. The tablet according to claim 12, further comprising the second barrier layer laminated to the opposite face of the matrix layer, wherein the second barrier layer is selected from nonswellable wax or polymeric material insoluble in aqueous medium.

16. The tablet according to claim 13, further comprising the second barrier layer laminated to the opposite face of the matrix layer, wherein the second barrier layer is selected from polymeric materials exhibiting a high degree of swelling and gelling in aqueous medium.

17. The tablet according to claim 13, further comprising the second barrier layer laminated to the opposite face of the matrix layer, wherein the second barrier layer is selected from nonswellable wax or polymeric material insoluble in aqueous medium.

18. The tablet according to claim 1, wherein the active agent is selected from the group consisting of bronchodilators, cough and cold agents, cognition enhancers.

19. The tablet according to claim 18, wherein the active agent is 2-methyl-3-(2-(S)-pyrroldinylmethoxy)pyridine.

* * * * *